United States Patent [19]

Laurer et al.

[11] 4,382,021

[45] May 3, 1983

[54] SUPPORTED CATALYST CONTAINING COPPER AND ALKALI METALS

[75] Inventors: Peter R. Laurer, Ludwigshafen; Gerd Krome, Weisenheim, both of Fed. Rep. of Germany; Luc Cordemans, Kapellen, Belgium; Reinhard Seifert; Eckehard Danz, both of Ludwigshafen, Fed. Rep. of Germany

[73] Assignee: BASF Aktiengesellschaft, Fed. Rep. of Germany

[21] Appl. No.: 324,983

[22] Filed: Nov. 25, 1981

[30] Foreign Application Priority Data

Dec. 10, 1980 [DE] Fed. Rep. of Germany ....... 3046407

[51] Int. Cl.$^3$ .............................................. B01J 27/10
[52] U.S. Cl. ................................... 252/441; 570/243; 570/246
[58] Field of Search ............... 252/441, 476; 570/243, 570/245

[56] References Cited

U.S. PATENT DOCUMENTS 3,210,431 10/1965 Engel .................................. 570/243

FOREIGN PATENT DOCUMENTS 2356549 10/1975 Fed. Rep. of Germany .
1104666 2/1968 United Kingdom .

Primary Examiner—W. J. Shine
Attorney, Agent, or Firm—Keil & Witherspoon

[57] ABSTRACT

A supported catalyst containing copper and alkali metals, wherein the content of copper is from 1.0 to 12% by weight, based on total catalyst and expressed as metal, and the total content of the alkali metals potassium, lithium and sodium is from 0.3 to 9% by weight, based on total catalyst.

The novel catalyst is useful for the preparation of 1,2-dichloroethane by oxychlorination of ethylene.

1 Claim, No Drawings

SUPPORTED CATALYST CONTAINING COPPER AND ALKALI METALS

The present invention relates to a supported catalyst containing copper and alkali metals, which is useful for the preparation of 1,2-dichloroethane by oxychlorination of ethylene.

The relevant prior art includes (1) British Pat. No. 1,104,666 and (2) German Pat. No. 2,356,549.

The oxychlorination of ethylene is a well known industrial process. In some embodiments, the oxychlorination is carried out in one reactor only. In that case, the requisite oxygen, together with HCl and ethylene, is passed through a single catalyst bed, which is operated substantially isothermally by suitable removal of heat. Publication (1) describes the reaction of ethylene with hydrogen chloride and oxygen in a plurality of reactors arranged in series, the oxygen, divided into a plurality of streams, being fed separately to each reactor. The reactors are charged with a catalyst which essentially contains copper chloride, or copper oxychloride, precipitated on a carrier. In a particular embodiment of the conventional process, the reactors are divided into zones of different catalyst activity.

The catalysts for the said purpose may, in addition to copper chloride or copper oxychloride, contain promoters. In particular, the literature describes the chlorides of the alkali metals, of the alkaline earth metals, of silver, of zinc and of the rare earths, especially of cerium, as being suitable.

However, the known catalysts have the disadvantage that, whilst their activity is high, they have only a low selectivity. It is an object of the present invention to overcome the disadvantages of the known catalysts. We have found that this object is achieved with a catalyst as claimed in claim 1.

The catalyst according to the invention contains copper in amounts of from 1 to 12% by weight, based on total catalyst and calculated as metal. In preparing the catalyst, the copper is generally introduced in the form of copper chloride or copper oxychloride. Preferred copper contents are from 1.5 to 9% by weight, based on total catalyst and calculated as metallic copper.

The catalyst according to the invention additionally contains from 0.3 to 9% by weight of the alkali metals potassium, lithium and sodium. The combined content of the 3 alkali metals is preferably from 0.3 to 3% by weight and more especially from 0.5 to 1.5% by weight. Each of the alkali metals is used in an amount of from 0.1 to 3% by weight. Particularly preferred catalysts contain from 0.3 to 1.0% by weight of each of the alkali metals. All these percentages are based on total catalyst, with the alkali metals calculated as metal.

In preparing the catalyst, the alkali metals are preferably introduced in the form of the chlorides, ie. as potassium chloride, sodium chloride or lithium chloride; they are present in the catalyst in this form.

It is known to a skilled worker, in the context of the present invention, that he can prepare catalysts of lower activity by raising the weight ratio of the sum of alkali metals to copper chloride to values of up to 1:1, in order to prepare catalysts suitable for the entry zone, described in (1), where a high oxygen partial pressure prevails. The weight ratio of the sum of the alkali metals to copper can be chosen within wide limits, namely from 0.05 to 1.0.

In addition to the copper and alkali metal promotors, the catalyst comprises a carrier, and these together account for 100% of the total catalyst. The preferred carrier for the catalyst according to the invention is active alumina, $\gamma$-$Al_2O_3$ being the particularly preferred modification. However, carriers consisting of transition oxides of $Al_2O_3$, of mixtures of these oxides with $\alpha$-$Al_2O_3$, of mixtures of aluminas and silica, and of aluminum silicates, are also suitable. The catalyst carrier should be prepared, through selection of conditions known to a skilled worker, so that it has a specific surface area, measured by the BET method, of from 80 to 300 $m^2/g$, with pore volumes of from 0.4 to 1.0 $cm^3/g$. The choice of a suitable carrier for subsequent preparation of the caralyst is made according to principles known to a skilled worker.

Preferably, the catalyst is prepared by impregnating the carrier with an aqueous solution which contains appropriate concentrations of copper(II) salts, hydrogen chloride and alkali metal chloride. Depending on the desired content of copper and alkali metals, it may be possible to carry out the impregnation of the carrier in a single stage, and this is also the most advantageous and most economical method. However, there may be cases where a single impregnation will not suffice to apply the desired amount of metals to the carrier. The measures which a skilled worker has to take in order to apply the desired amount of metals to a carrier are known. The impregnation of the catalyst carrier, and the subsequent treatment of the impregnated carrier moldings, are described in detail in publication (2), column 3, lines 37–67.

The chosen shape of carrier also plays some part in determining the activity. Suitable carrier shapes include tablets, spheres or rings. Rings are particularly preferred and may, depending on the desired end use and the position in which the catalyst is employed, have an external diameter of 5–12 mm, an internal diameter of 3–8 mm, and a height of 3–12 mm.

To carry out the examples and comparative experiments I and II, the catalysts A, B and C described below were used:

Catalyst A corresponded to the catalyst of the example given in (2).

Catalyst B was prepared in accordance with the teaching of (2), using the chlorides of the alkali metals potassium and sodium, and was thus neither in accordance with the invention nor in accordance with the prior art.

Catalyst C is a catalyst according to the invention, prepared according to the process described in (2), using the chlorides of potassium, sodium and lithium.

To prepare the said 3 catalysts A, B and C, cylindrical tablets of size 5×5 mm, consisting of $\alpha$-$Al_2O_3$ having a specific surface area of 150 $m^2/g$ and a porosity (pore volume) of 0.75 $cm^3/g$ were used in each case. The composition of the catalyst is given below, all percentages being by weight, and the remainder of the composition being the carrier.

|   | % of Cu | % of K | % of Na | % of Li |
|---|---------|--------|---------|---------|
| A | 7.5     | 0.77   | —       | —       |
| B | 7.5     | 0.76   | 0.87    | —       |
| C | 6.9     | 0.74   | 0.90    | 0.87    |

The Examples and comparative experiments described below illustrate the invention. All parts and percentages are by weight, unless stated otherwise.

EXAMPLE 1 AND COMPARATIVE EXPERIMENTS I AND II

In the experiments described below, the catalysts A, B and C were tested in an isothermally operated tubular reactor, at 250° C., for the synthesis of 1,2-dichloroethane. The gas used for the reaction contained 6.1 percent by volume of HCl, 2.86 percent by volume of $C_2H_4$ and 1.71 percent by volume of $O_2$, the remainder being nitrogen, which was added to prevent overheating.

The sum of CO and $CO_2$, in percent by volume, was determined in the reactor exit gas. The sum of chlorohydrocarbons formed, in % by weight, and the ethylene conversion, were also determined.

The ethylene conversion is a measure of the activity of the catalyst. The amount of CO and $CO_2$ formed, due to the oxidation of ethylene, can be regarded as a measure of the selectivity of the catalyst. The same is true of the sum of the chlorohydrocarbons other than 1,2-dichloroethane, which are separated from the desired product by distillation or are isolated from the exit gas by condensation at low temperatures.

In Example 1 (using catalyst C) and Comparative Experiments I and II (using catalysts A and B respectively), the following values were found:

| Example/Comparative Experiment | I | II | 1 |
|---|---|---|---|
| Catalyst | A | B | C |
| Oxidation (% by vol. of CO + $CO_2$) | 0.263 | 0.059 | 0.036 |
| Chlorohydrocarbons (sic) (% by weight) | 0.707 | 0.402 | 0.307 |
| Ethylene conversion | 87.8 | 88.8 | 88.1 |

A comparison of the results shows that for roughly similar activity, catalyst C, according to the invention, exhibits substantially improved selectivity over the prior art catalyst A, and over catalyst B, which is not prior art.

We claim:

1. A supported catalyst which is useful for the oxychlorination of ethylene and which comprises: a carrier and deposited therein
   (a) copper in the form of copper chloride or copper oxychloride, the amount of copper calculated as metal being from 1.0 to 12% by weight based on the total catalyst, and
   (b) alkali metals in the form of potassium chloride, sodium chloride and lithium chloride, the total content of the alkali metals based on the total catalyst being from 0.3 to 9% by weight.

* * * * *